United States Patent
Haikarainen et al.

(10) Patent No.: US 6,769,601 B2
(45) Date of Patent: Aug. 3, 2004

(54) INHALER WITH A DOSE COUNTER

(75) Inventors: Jussi Haikarainen, Espoo (FI); Kari Seppälä, Helsinki (FI); Jarkko Munukka, Espoo (FI); Esa Muttonen, Espoo (FI); Elizabeth Stares, Nether Broughton (GB); Martin Murphy, Letchworth (GB); Matthew Young, Over (GB)

(73) Assignee: Orion Corporation, Espoo (FI)

( * ) Notice: Subject to any disclaimer, the term of this patent is extended or adjusted under 35 U.S.C. 154(b) by 0 days.

(21) Appl. No.: 10/276,145

(22) PCT Filed: May 16, 2001

(86) PCT No.: PCT/FI01/00479
§ 371 (c)(1),
(2), (4) Date: Jul. 16, 2003

(87) PCT Pub. No.: WO01/87391
PCT Pub. Date: Nov. 22, 2001

(65) Prior Publication Data
US 2004/0089298 A1 May 13, 2004

(30) Foreign Application Priority Data
May 17, 2000 (GB) .............................................. 0011739

(51) Int. Cl.$^7$ ................................................. G06C 3/00
(52) U.S. Cl. ...................... 235/87 R; 235/77; 235/87 A
(58) Field of Search .............................. 235/50 R, 50 A, 235/50 B, 77, 87 R, 87 A; 128/200.12, 200.14, 200.18, 200.23, 200.24, 200.22, 205.23, 203.15

(56) References Cited

U.S. PATENT DOCUMENTS

| | | | | |
|---|---|---|---|---|
| 5,349,945 A | * | 9/1994 | Wass et al. ............. | 128/200.23 |
| 5,482,030 A | * | 1/1996 | Klein ..................... | 128/200.23 |
| 5,564,414 A | * | 10/1996 | Walker et al. ......... | 128/200.23 |
| 5,575,280 A | | 11/1996 | Gupte et al. | |
| 5,988,496 A | | 11/1999 | Bruna | |
| 6,446,627 B1 | * | 9/2002 | Bowman et al. ....... | 128/200.23 |
| 6,553,987 B1 | * | 4/2003 | Davies ................... | 128/200.14 |

FOREIGN PATENT DOCUMENTS

| | | |
|---|---|---|
| WO | WO 95/34874 | 12/1995 |
| WO | WO 97/30743 | 8/1997 |
| WO | WO 98/28033 | 7/1998 |
| WO | WO 01/37909 | 5/2001 |

\* cited by examiner

*Primary Examiner*—Karl D. Frech
(74) *Attorney, Agent, or Firm*—Finnegan, Henderson, Farabow, Garrett & Dunner, LLP

(57) ABSTRACT

A multiple-dose powder inhaler comprising an inhaler body defining a medicament container, an air channel, a mouthpiece, a rotatable metering drum with one or more peripheral dosing recesses and a dose counter for indicating the number of metered doses of medicament that have been dispensed from, or remain in, the medicament container. The inhaler is useful, for example, in the treatment of asthma.

13 Claims, 5 Drawing Sheets

INHALER WITH A DOSE COUNTER

This application is a national stage filing of PCT International Application No. PCT/FI01/00479, filed on May 16, 2001. This application also claims the benefit of priority under 35 U.S.C. §119(a) to GB patent application no. 0011739.0, filed on May 17, 2000.

BACKGROUND OF THE INVENTION

The present invention relates to an inhaler device for dispensing medicament by inhalation. In particular the invention relates to a multiple-dose dry powder inhaler having a dose counter for indicating the number of metered doses of medicament that have been dispensed from, or remain in, the medicament container of the inhaler device.

The administering of a powdered drug preparation by inhalation from an inhaler device is known. Typical inhalation devices include pressurized metered dose inhalers (pMDI) having a canister with particulate medicament suspended in propellant gas and dry powder inhalers (DPI) having a container of powdered medicament without propellant gas.

Various dose counters have been described which are intended for use in pressurized metered dose inhalers or dry powder inhalers. The dose counters generally help the patient to keep track of the number of doses still available from the inhaler device and thereby warn the patient when the inhaler nears exhaustion. The dose counters usually have in common the feature that they detect the relative movement between the medicament container and the actuating or dosing member, and increment in response to such movement For example, International patent publication WO 86/05991 describes a multiple-dose powder inhaler having a dose counter comprising a counting wheel vertically mounted above a horizontally mounted perforated dosing disc said counting wheel being rotated by a worn drive forming part of the rotatable dosing disc.

International patent publication WO 97/20589 describes a multiple-dose powder inhaler with a dose counter comprising a co-axially mounted set of units wheel, tens wheel and hundreds wheel, wherein the units wheel is driven by a spring leaf connected to a longitudinally movable dosing slide.

International patent publication WO 92/00771 describes a multiple-dose powder inhaler having a rotatable dosing member and a dose counter comprising a tape secured to the axle of the metering member the tape being wound onto said axle upon rotation of the metering member. In another embodiment the dose counter comprises a counting ring and a driving disc arranged co-axially with the metering member the driving disc being equipped with a spring arm. When the driving disc completes one rotation, the spring arm cooperates with a cam secured to the housing and engages with the counting disc.

U.S. Pat. No. 5,687,710 describes a multiple-dose powder inhaler having a rotatable dosing plate and a dose counter comprising a continuous and intermittent counter rings. The counter rings are co-axially mounted and have counting indicia on their outer surfaces. An actuating means has a pawl for engaging with the gear teeth of the continuous and intermittent counter rings.

European patent publication EP 488609 describes a multiple-dose powder inhaler having a longitudinally movable dosing member and a dose counter comprising an actuating finger for rotating an indexing gear. The indexing gear is connected via a worm drive to a gear wheel equipped with counting indicia.

International patent publication WO 94/11044 describes a multiple-dose powder inhaler having a rotatable dosing member and a dose counter comprising a ratchet wheel cooperating with the actuating means, an eccentric orbital gear and a cover plate having counting indicia thereon.

The above constructions have a drawback that they are bulky or have complex moving parts which can be difficult to assemble and expensive to manufacture.

A multiple-dose dry powder inhaler sold under the trademark Easyhaler comprises a counter wheel having gear teeth and counting indicia the counter wheel being driven by a pin extending from a rotatable metering member. The counter wheel is rotatably mounted on two arcuate bearing ribs, which match a circular groove formed near the periphery of the counter wheel. Whilst the construction is simple and compact, it has a drawback that the counter wheel is susceptible to unintentional movements or jamming, as the bearing ribs have a double function of bearing and braking the counter wheel.

There is need for a powder inhaler having a dose counter which avoids the above disadvantages. In particular, the counter unit should comprise a relatively few, simple mechanical parts, should not require excessive amounts of space and should provide at the same time reliable counting function.

SUMMARY OF THE INVENTION

The present invention provides a multiple-dose powder inhaler for dispensing powdered medicament by inhalation comprising an inhaler body defining a medicament container for receiving a plurality of powdered medicament doses;

an air channel through which air is drawn via a mouthpiece;

a metering drum rotatable about its rotational axis and having one or more peripheral dosing recesses for receiving in one position a metered dose of the powdered medicament from the medicament container and for bringing in another position the metered dose of the powdered medicament to the air channel; and a dose counter for indicating the number of metered doses of medicament that have been dispensed from, or remain in, the medicament container, said dose counter comprising a counter wheel having a central hole said counter wheel being rotatably mounted about a bearing axle having a longitudinal axis substantially parallel to and spaced from the rotational axis of the metering drum, said bearing axle extending from the inhaler body and though the central hole, and said counter wheel having counting indicia thereon and a plurality of gear teeth;

extending from the metering drum a driving pin adapted to engage with at least one of said plurality of gear teeth of the counter wheel upon every complete revolution of the metering drum so as to rotate said counter wheel an incremental amount; and a flexible brake finger extending from the inhaler body and adapted to engage with the counter wheel so as to maintain a unidirectional rotation and to prevent unintentional movement of the counter wheel.

The dose counter of the present invention detects the stepwise rotation of the metering drum between a loading position, wherein the dosing recess of the metering drum is loaded with a dose of medicament, and the inhalation position, wherein the filled dosing recess is brought to the air channel. Preferably the stepwise rotation of the metering drum is achieved by means of a ratchet wheel. The ratchet wheel is suitably co-axial and integrated with the metering drum into a one-piece component.

The ratchet wheel of the metering drum can be manually operated. Preferably the ratchet wheel of the metering drum is driven by a longitudinally movable actuating member. For example, the inhaler can be actuated by means of an axial movement of a depressible cover. In such embodiment the depressible cover may comprise an elongate pawl adapted to engage with the ratchet wheel of the metering drum upon each axial movement of the cover. A complete revolution of the metering drum is then accomplished by making a predetermined number of said axial movements of the cover, such number being dependent on the number of teeth in the ratchet wheel.

The counter wheel is provided with a plurality of gear teeth and comprises preferably a relatively flat top portion having counting indicia, typically alpha-numerical characters, placed thereon. The gear teeth can be configured in the counter wheel in a suitable way such as to the outer periphery. In a preferred embodiment the counting wheel comprises a circumferential skirt portion and the gear teeth are formed around the inner circumference of the skirt such that the gear teeth are facing inwardly towards the axis of the counter wheel.

The counter wheel is rotatably mounted on a bearing axle extending from the inhaler body. In a preferred embodiment the bearing axle extends from the outer wall of the medicament container. The counter wheel has a central hole through which the bearing axle extends, such that the counter wheel is supported by the bearing axle. The counter wheel is disposed adjacent to the metering drum in such a way that the rotational axis of the counter wheel is substantially parallel to but spaced from the rotational axis of the metering drum.

The counter wheel is driven by a pin extending from the flat surface of the metering drum in the direction of the counter wheel. The portion of the pin engaging with the gear teeth of the counter wheel is generally set off from the axis of the metering drum such that the engagement occurs only upon every complete revolution of the metering drum. The pin can also be configured as a gear wheel extending co-axially with the metering drum, wherein all other teeth of the gear wheel except one are cut away. In such embodiment the one remaining tooth of the gear wheel acts as the driving pin. In operation, the driving pin is adapted to engage with at least one of the gear teeth of the counter wheel upon every complete revolution of the metering drum so as to rotate said counter wheel an incremental amount. Said incremental amount is generally depending on the number of teeth in the counter wheel. The predetermined number of axial movements of the depressible cover required to cause the counter wheel to rotate a complete revolution depends on the number of teeth in the ratchet wheel and the counter wheel. Typically it is intended that the counter wheel makes only one single revolution during the lifetime of the inhaler.

Preferably the inwardly facing teeth are formed around only a portion of the inner circumference of the skirt of the counter wheel such that a gap is formed therebetween. This ensures that the counter wheel cannot be advanced past the last indicia indicating that the container is empty.

The flexible brake finger extending from the inhaler body is preferably adapted to engage with at least one of said plurality of gear teeth of the counter wheel. In a preferred embodiment of the invention the flexible brake finger is adapted to engage simultaneously with the engagement portion of at least two non-adjacent gear teeth of the counter wheel. This ensures that the counter wheel is not susceptible to unintentional movements, and in particular that the counter wheel is steady also in such position where the brake finger encounters said gap between the teeth of the counter wheel.

It is also possible to configure the flexible brake finger such that it engages with additional gear wheel, which is disposed e.g. on the outer periphery of the counter wheel. In such embodiment the counter wheel is provided with two gear wheels, one for the incremental rotation by the driving pin and one for the engagement by the brake finger.

Preferably the flexible brake finger is configured as having two curved surfaces, for the engagement simultaneously with a engagement surface of at least two non-adjacent gear teeth, and a bridge connecting said curved surfaces.

DETAILED DESCRIPTION OF THE INVENTION

The device of the invention is illustrated below by way of example, with reference to FIGS. 1 to 7.

Figure 1:
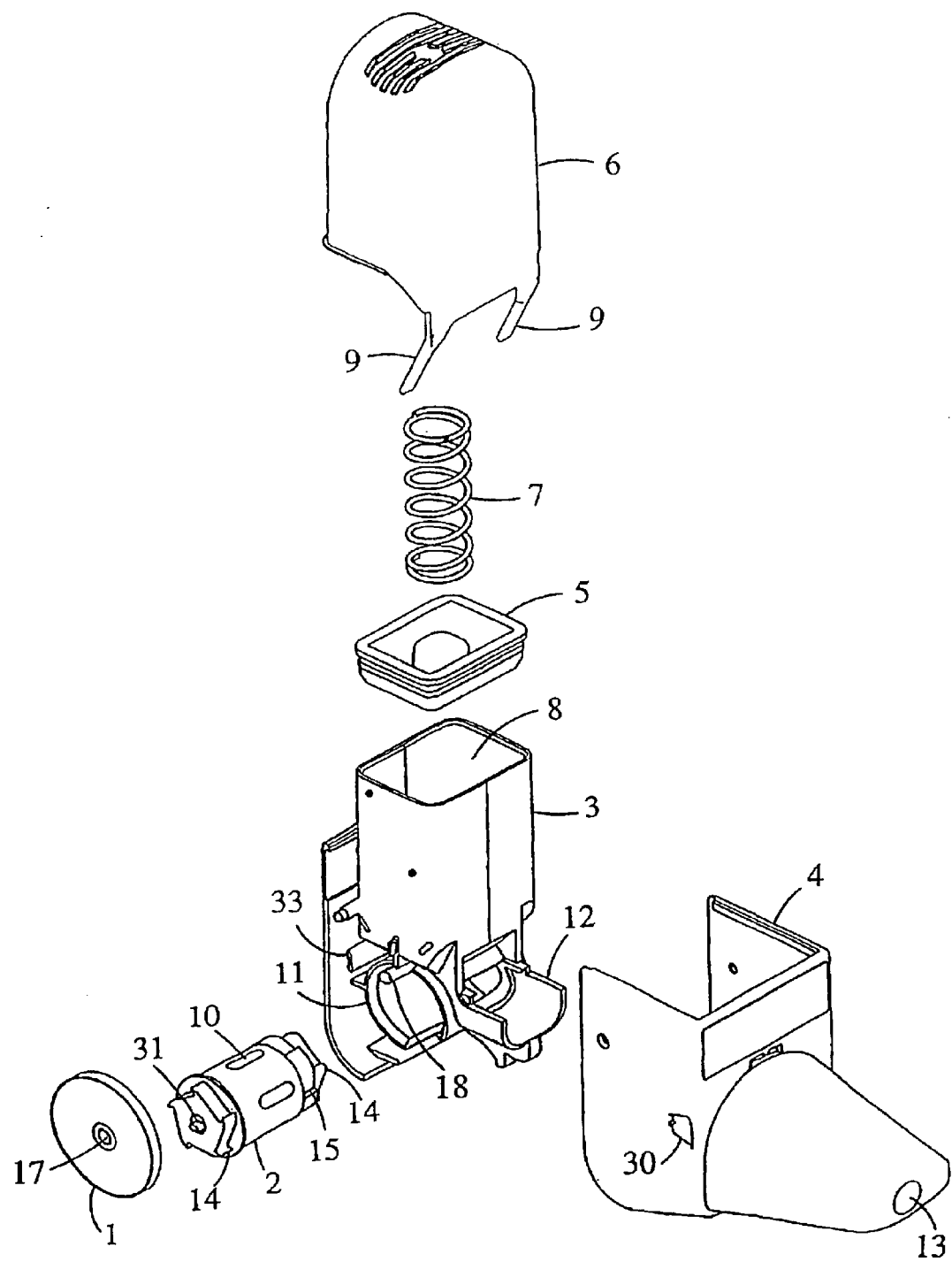
FIG. 1 is an explosive perspective view of one embodiment of the device of the invention.

In FIG. 1 the structure of one embodiment of the device of the invention is shown in an explosive view. The main parts of the device are a body (3), a mouthpiece (4), a depressible cover (6), a metering drum (2) and a counter wheel (1). The body (3), also shown in FIGS. 3 and 4, defines a medicament container (8), which is to be filled with a powdered medicament. The container (8) has a square cross-section and a conical end portion. A lid (5) closes the upper edge of the medicament container. The depressible cover (6) together with a pair of elongate pawls (9), the function of which will be explained below, is adapted to cover the medicament container (6) and the lid (5). A spring (7) urges the depressible cover (6) in its upper (rest) position. A rotatable metering drum (2) having five dosing recesses (10) is mounted to the hollow cylindrical element (11), which is moulded together with the medicament container (8). Typically, the container has a supply of medicament for e.g. 200 doses.

The body (3) also defines the rear wall (9) of the device as well as the projection (12) to receive the mouthpiece (4) with the air channel (13). The vertical walls of the mouthpiece serve as side walls of the device. On one vertical wall of the mouthpiece (4) a window (30) is provided through which part of the counter wheel (1) is visible. From the wall

(32) connecting the rear wall and the medicament container (8) extends a flexible braking finger (33), the function of which will be explained below.

The metering drum (2) has, in addition to the series of dosing recesses (10), two series of five ratchet teeth (14) adapted to engage with the elongate pawls (9) of the cover (6). The ratchet teeth (14) and the metering drum are molded as one-piece component. The device is actuated by pressing down the cover (6), whereby the pawls (9) engaging with the teeth (14) cause the metering drum in (2) rotate so that rotation can only be accomplished stepwise corresponding to the peripheral distance between the dosing recesses (10). Furthermore, the cylindrical element (11) has an extended detent nose (16), better shown in FIG. 3, adapted to engage with notches (15) in the metering drum (2) such that the rotation is possible only to one direction. The detent nose (16) automatically aligns the dosing recesses (10) with the outlet of the medicament container (8) on the one side and the air channel (13) of the mouthpiece (4) on the other side.

A counter wheel (1), the function of which will be explained below, equipped with a central hole (17) is rotatably mounted on a bearing axle (18) extending from the body (3) of the inhaler.

Figure 2:
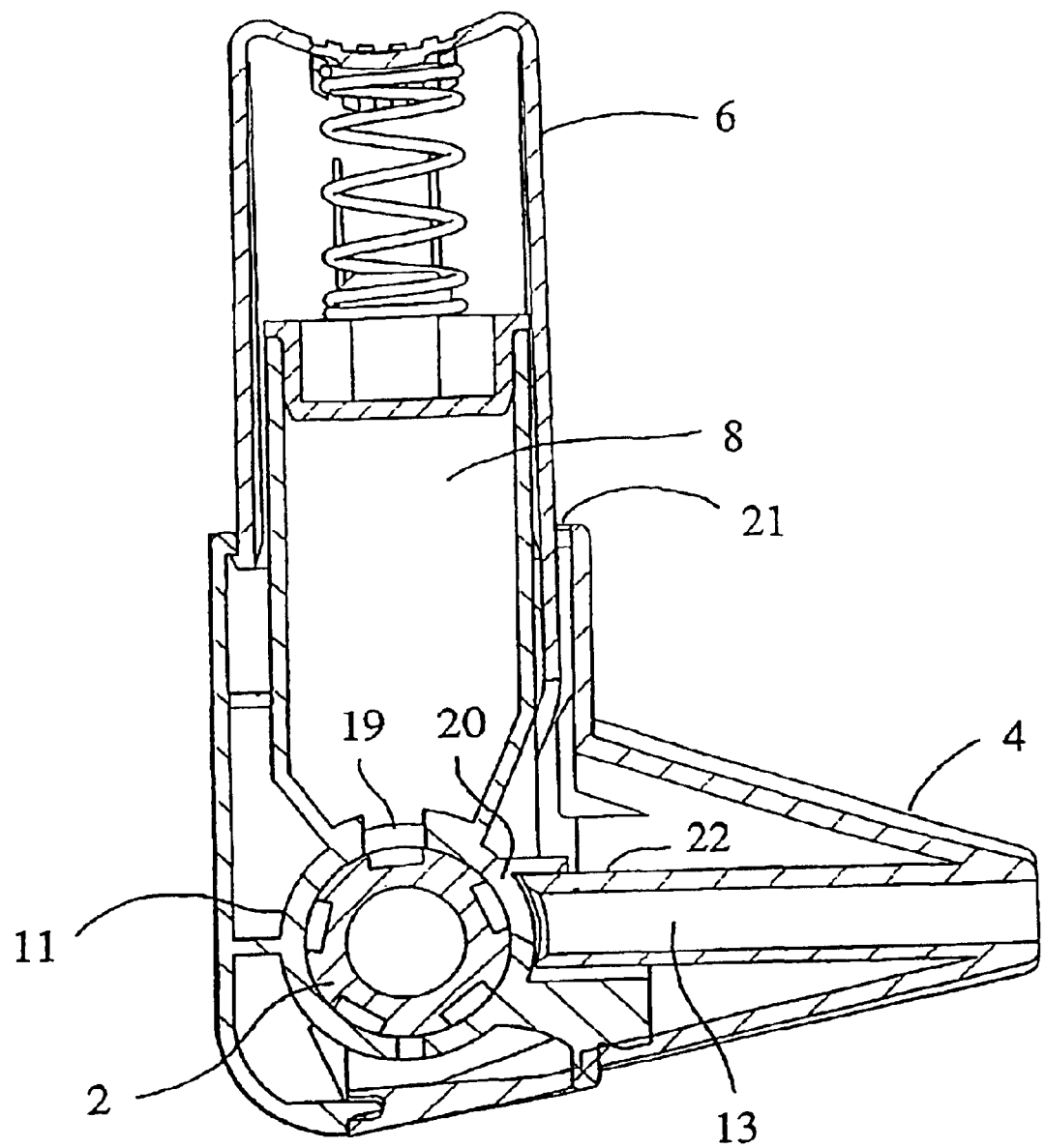
FIG. 2 is a longitudinal section of the device of FIG. 1 through the medicament container.
Figure 3:
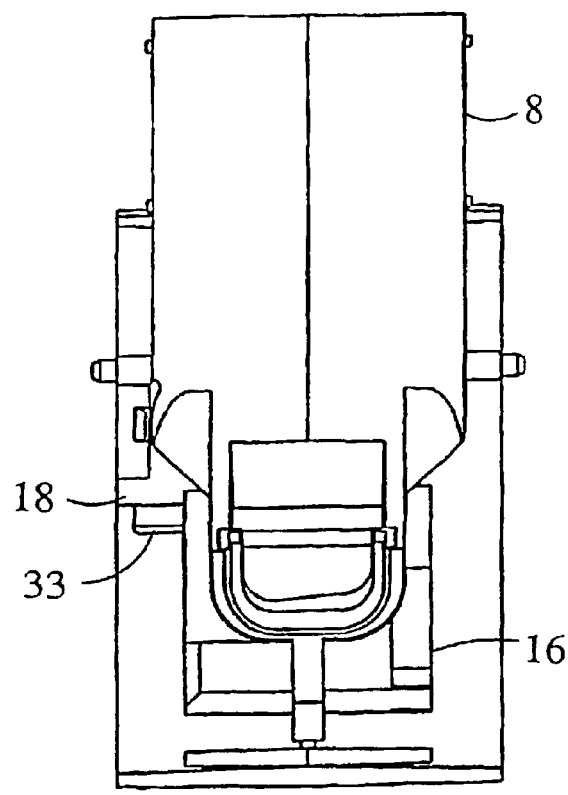
FIG. 3 is a front view of the body component of the inhaler of FIG. 1.
Figure 4:
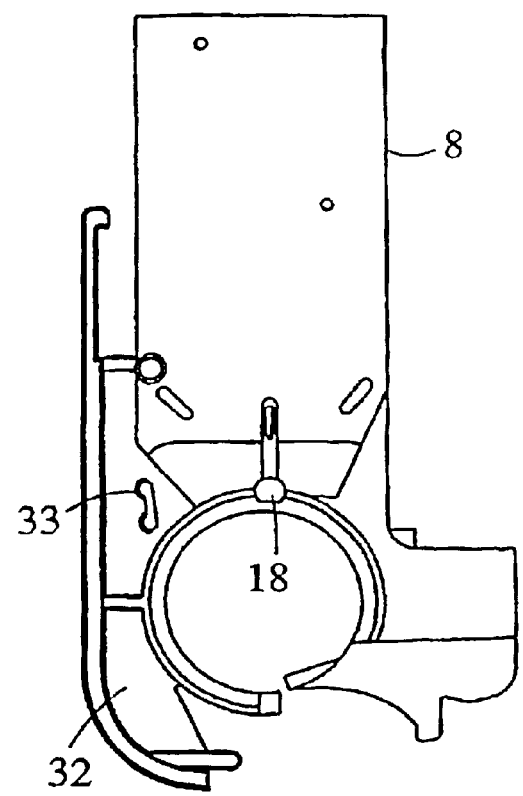
FIG. 4 is a side view of the body component of the inhaler of FIG. 1.

FIG. 2 shows a longitudinal section through the medicament container (8) of the device. The cylindrical body (11) has an opening (19) through which powder can fall from the medicament container (8) to the dosing recess (10) when the dosing recess is in alignment with the opening (19). Another opening (20) is provided at the level of the air channel (13) for discharging the powder from the dosing recess to the air channel (13) upon inhalation. In the position shown in FIG. 2 the upper dosing recess is just being filled with the dose of the powdered medicament from the medicament container (8), while the earlier filled dosing recess has turned to the air channel (13) the dose being ready for inhalation. The mouthpiece (4), through which the powder can be inhaled, is formed at one side of the inhaler device and has an air channel (13) for distribution of the dose of medicament from the dosing recess into the flow of breathing air. In the area where the mouthpiece (4) is attached, air intakes (21) are provided. The intaken air is led to a slot between the opening (20) of the cylindrical element (11) and a partition wall (22) of the mouthpiece (4). The slot provides strongly aligned stream of air to the dosing recess blowing the powder out from the dosing recess into the air channel (13).

Figure 5:
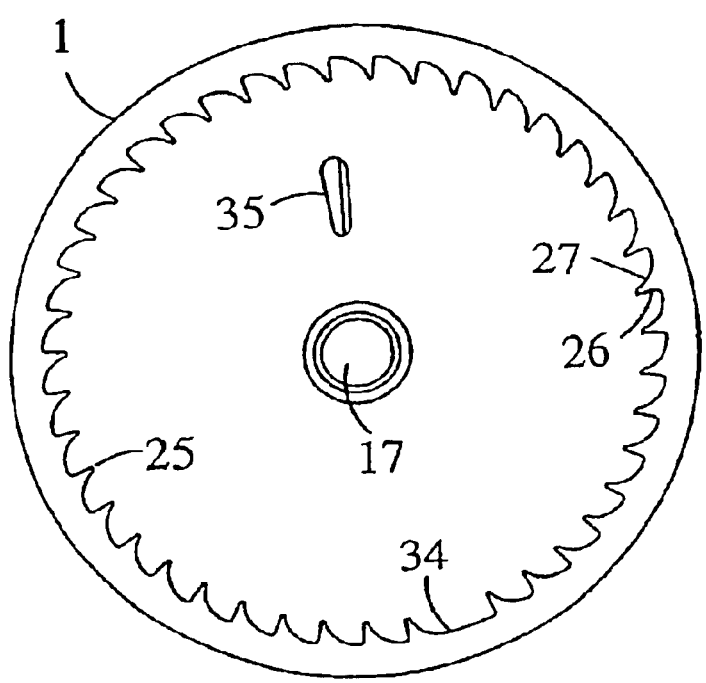
FIG. 5 is a bottom view of the counter wheel of the inhaler of FIG. 1.
Figure 6:
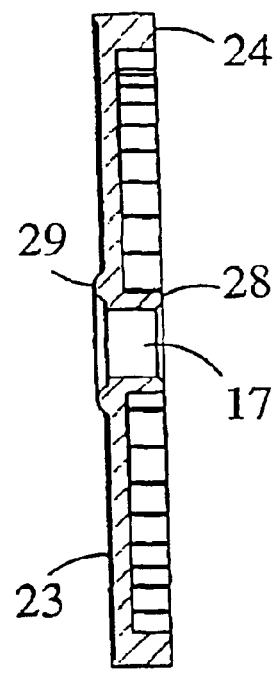
FIG. 6 is a cross-sectional view of the counter wheel of FIG. 4.
Figure 7:
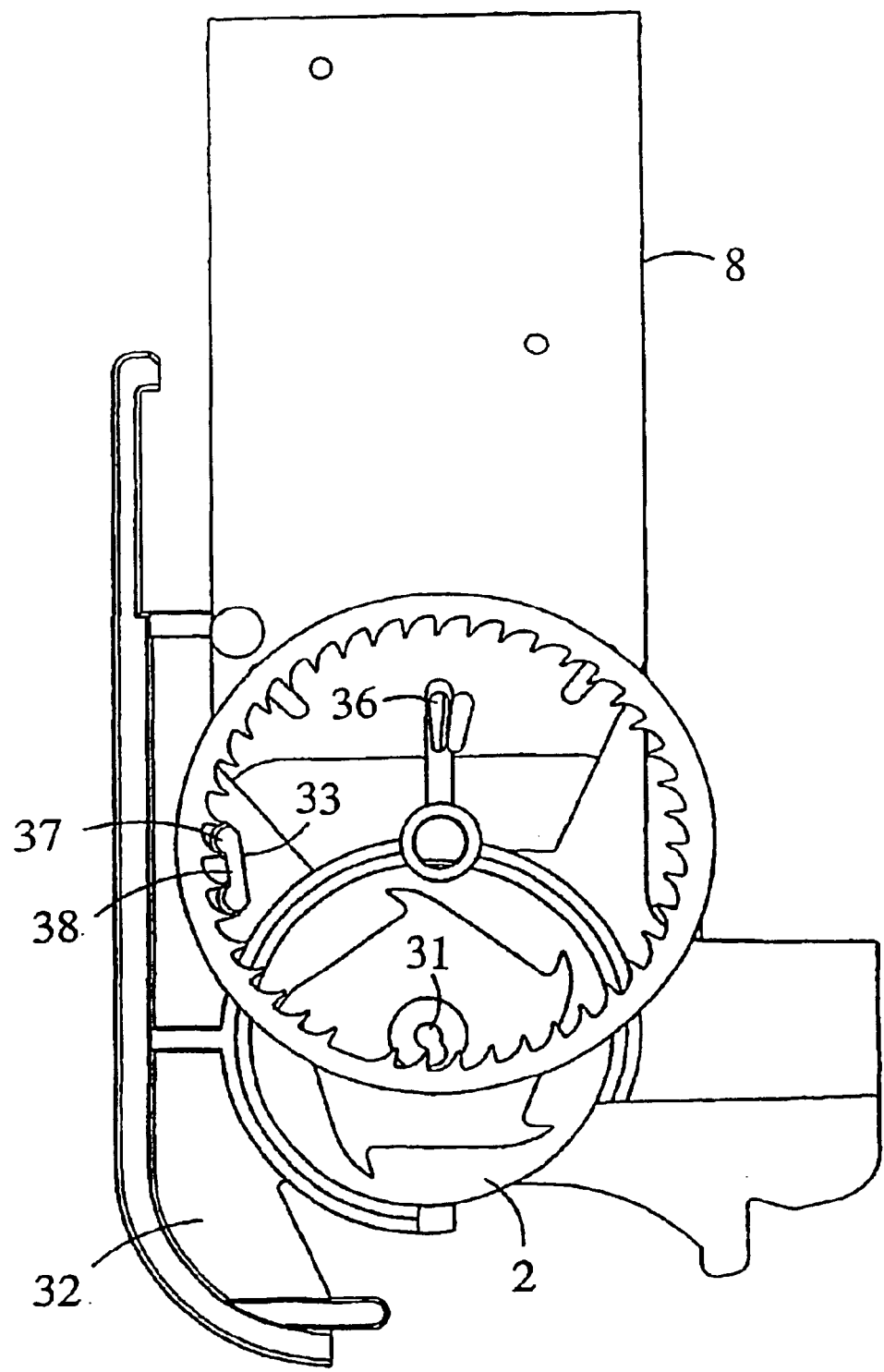
FIG. 7 is a side view of the body component, counter wheel and the metering drum of the inhaler of FIG. 1 assembled together, wherein the components are depicted as being transparent.

Referring now to FIGS. 5–7, the structure of the dose counter of the device is explained. The bottom and cross-sectional views of the counter wheel (1) are shown in FIGS. 5 and 6. The counter wheel has a flat top portion (23) and a circumferential skirt portion (24). A plurality of gear teeth (25) are formed around the inner circumference of the skirt portion (24) such that the gear teeth (25) are facing inwardly towards the axis of the counting wheel. Each gear tooth (25) comprises a shoulder portion (26) and a tapered portion (27). Counting indicia (not shown), e.g. multiple of tens, are placed on the relatively flat top portion (23) of the counting wheel (1) such that part of the indicia are visible through the window (30). The counter wheel (1) is provided with a central hole (17) extending through the counter wheel (1) and an aligned boss (28) for supporting the counter wheel (1) on the bearing axle (18). On the top portion (23) there is a protruding ring (29) for a sliding contact with the vertical wall of the mouthpiece (4).

FIG. 7 is a side view of the body (3), counter wheel (1) and the metering drum (2) assembled together, wherein the components are depicted as being transparent. The metering drum (2) is inserted in the cylindrical element (11). The metering drum is provided with a driving pin (31), which extends axially from the flat surface of the metering drum (2) in the direction of the counter wheel (1). The driving pin (31) is in the form of a small diameter gear wheel extending co-axially with the metering drum (2), wherein all other teeth of the gear wheel except one have been cut away.

The counter wheel (1) is rotatably mounted on the bearing axle (18), which extends from the rim of the cylindrical element (11) in the vicinity of the outer wall of the medicament container (8). The central hole (17) and the aligned boss (28) of the counter wheel (1) is adapted to receive the bearing axle (18) such that the head of the bearing axle (18) extends to the level of the top portion (23) of the counter wheel (1). It is to be noted that the counter wheel (1) is disposed adjacent to the metering drum (2) in such a way that the rotational axis of the counter wheel (1) is substantially parallel to but spaced from the rotational axis of the metering drum (2).

As shown by FIG. 7 the tooth of the driving pin (31) is adapted to engage with a shoulder portion (26) of the gear teeth (25) of the counter wheel (1). The portion of the driving pin (31) engaging with the gear teeth (25) is set off from the axis of the metering drum (2) such that the engagement occurs only upon every complete revolution of the metering drum (2). As the metering drum has five ratchet teeth (14), the metering drum (2) makes one complete rotation after five axial movements (actuations) of the depressible cover (6). Thus, the driving pin (31) engages with one of the gear teeth (25) of the counter wheel (1) upon every fifth actuations and rotates the counter wheel (1) an incremental amount. Said incremental amount depends on the number of gear teeth (25) in the counter wheel (1). The predetermined number of the axial movements of the depressible cover (6) required to cause the counter wheel (1) to rotate a complete revolution depends on the number of ratchet teeth (14) in the metering drum (2) and the gear teeth (25) of the counter wheel (1). In the figuration of FIG. 7 more than 200 actuations are needed to rotate the counter wheel (1) one complete revolution.

As best shown in FIG. 5, the gear teeth (25) are formed around only a portion of the inner circumference of the skirt (24) of the counter wheel (1) such that a gap (34) is formed therebetween. After the driving pin (31) has engaged with the last gear teeth (25) before the gap (34), the driving pin (31) is not able to rotate the counter wheel (1) upon next or subsequent rotations. This ensures that the counter wheel (1) cannot be advanced by repeated actuations past the last indicia indicating that the medicament container (8) is empty. Furthermore, the rotation of the counter wheel (1) past the last indicia is prevented by means of a stopper pin (35) adapted to engage with a projection (36) extending from the outer wall of the medicament container (8).

A brake finger (33), slightly flexible in the direction of the bearing axle (18), extends from the body (3) and has a longitudinal axis parallel to the rotational axis of the counting wheel (1). The flexible brake finger (33) is adapted to engage with the gear teeth (25) of the counter wheel (1) so as to maintain a unidirectional rotation and to prevent unintentional movement of the counter wheel (1). The engaging portion of the brake finger (33) is configured such that it can engage simultaneously with the shoulder portion (26) of two non-adjacent gear teeth (25) of the counter wheel (1). This ensures that the counter wheel (1) is steady also in such position where the brake finger (33) encounters the gap (34) between the teeth of the counter wheel. This is accomplished by shaping the engaging portion of the brake finger

(33) into the form of two curved surfaces (37) and a bridge (38) connecting the surfaces (37).

Those skilled in the art will recognize that modifications and variations can be made in form and detail to the disclosed embodiments without departing from the spirit and scope of the invention as defined in the following claims. It is considered to be routine for one skilled in the art to make such modifications to the device of the invention.

What is claimed is:

1. A multiple-dose powder inhaler for dispensing powdered medicament by inhalation comprising
   an inhaler body defining a medicament container for receiving a plurality of powdered medicament doses;
   an air channel through which air can be drawn via a mouthpiece;
   a metering drum rotatable about its rotational axis and having one or more peripheral dosing recesses for receiving in one position a metered dose of powdered medicament from the medicament container and for bringing in another position a metered dose of powdered medicament to the air channel; and
   a dose counter for indicating the number of metered doses of medicament that have been dispensed from, or remain in, the medicament container, said dose counter comprising
   a counter wheel having a central hole, said counter wheel being rotatably mounted about a bearing axle having a longitudinal axis substantially parallel to and spaced from the rotational axis of the metering drum, said bearing axle extending from the inhaler body and through the central hole, and said counter wheel having counting indicia thereon and a plurality of gear teeth;
   extending from the metering drum a driving pin adapted to engage with at least one of said plurality of gear teeth of the counter wheel upon every complete revolution of the metering drum so as to rotate said counter wheel an incremental amount; and
   a flexible brake finger extending from the inhaler body and adapted to engage with the counter wheel so as to maintain a unidirectional rotation and to prevent unintentional movement of the counter wheel.

2. An inhaler of claim 1, wherein the flexible brake finger is adapted to engage with at least one of said plurality of gear teeth of the counter wheel.

3. An inhaler of claim 1, wherein the flexible brake finger is adapted to engage simultaneously with the engagement portion of at least two non-adjacent gear teeth of the counter wheel.

4. An inhaler of claim 3, wherein the flexible brake finger has two curved surfaces, for the engagement simultaneously with the engagement portion of at least two non-adjacent gear teeth, and a bridge connecting said curved surfaces.

5. An inhaler of claim 1, wherein the periphery of the counter wheel has a top portion and a circumferential skirt.

6. An inhaler of claim 5, wherein the gear teeth of the counter wheel are in the form of inwardly facing teeth formed around the inner circumference of the skirt.

7. An inhaler of claim 6, wherein the inwardly facing teeth are formed around only a portion of the inner circumference such that a gap is formed therebetween.

8. An inhaler of claim 1, wherein said counting indicia are placed on the top portion of the counter wheel.

9. An inhaler of claim 1, wherein the bearing axle extends from the outer wall of the medicament container.

10. An inhaler of claim 1, wherein the metering drum comprises integrated ratchet teeth for the stepwise rotation of the metering drum.

11. An inhaler of claim 1, comprising a depressible cover for actuating the inhaler by an axial movement of the depressible cover.

12. An inhaler of claim 11, wherein the depressible cover comprises an elongate pawl adapted to engage with the ratchet teeth of the metering drum upon each axial movement of the depressible cover.

13. An inhaler of claim 11, wherein said complete revolution of the metering drum is accomplished by making a predetermined number of said axial movements of the depressible cover.

* * * * *